(12) United States Patent
Stevens

(10) Patent No.: US 6,616,651 B1
(45) Date of Patent: Sep. 9, 2003

(54) INTRAVASCULAR MICROCATHETER WITH EMBEDDED HELICAL COIL REINFORCEMENT MEMBER AND METHODS AND APPARATUS FOR MAKING SAME

(76) Inventor: Robert C. Stevens, 7827 SW. 43rd Dr., Gainesville, FL (US) 32608

( * ) Notice: Subject to any disclaimer, the term of this patent is extended or adjusted under 35 U.S.C. 154(b) by 0 days.

(21) Appl. No.: 09/715,988

(22) Filed: Nov. 17, 2000

(51) Int. Cl.$^7$ .............................................. A61M 25/00
(52) U.S. Cl. .................... 604/524; 604/103.09; 606/194
(58) Field of Search ........................... 604/103.09, 524; 606/194

(56) References Cited

U.S. PATENT DOCUMENTS

| | | |
|---|---|---|
| 243,396 A | 6/1881 | Pfarre |
| 2,211,975 A | 8/1940 | Hendrickson |
| 3,485,234 A | 12/1969 | Stevens |
| 3,585,707 A | 6/1971 | Stevens |
| 3,720,235 A | 3/1973 | Schrock |
| 3,945,867 A | 3/1976 | Heller, Jr. et al. |
| 3,988,189 A | 10/1976 | Sullivan |
| 4,321,226 A | 3/1982 | Markling |
| 4,430,083 A | 2/1984 | Ganz et al. |
| 4,498,473 A * | 2/1985 | Gereg .................. 604/103.09 |
| 4,577,543 A | 3/1986 | Wilson |
| 4,665,604 A | 5/1987 | Dubowik |
| 4,737,153 A | 4/1988 | Shimamura et al. |
| 4,904,431 A | 2/1990 | O'Maleki |
| 4,981,478 A | 1/1991 | Evard et al. |
| 5,135,516 A | 8/1992 | Sahatjian et al. |
| 5,176,660 A | 1/1993 | Truckai |
| 5,244,619 A | 9/1993 | Burnham |
| 5,313,967 A | 5/1994 | Lieber et al. |
| 5,514,236 A | 5/1996 | Avellanet et al. |
| 5,560,103 A | 10/1996 | Harris et al. |
| 5,662,622 A | 9/1997 | Gore et al. |
| 5,667,499 A | 9/1997 | Welch et al. |
| 5,702,373 A | 12/1997 | Samson |
| 5,733,400 A | 3/1998 | Gore et al. |
| 5,738,742 A | 4/1998 | Stevens |
| 5,972,143 A | 10/1999 | Stevens |
| 6,152,912 A | 11/2000 | Jansen et al. |

FOREIGN PATENT DOCUMENTS

| | | |
|---|---|---|
| EP | 0 086 498 | 8/1983 |
| FR | 2 454 907 | 11/1980 |
| WO | WO 93/15785 | 8/1993 |

\* cited by examiner

*Primary Examiner*—Ronald Capossela
(74) *Attorney, Agent, or Firm*—Fay, Sharpe, Fagan, Minnich & McKee, LLP

(57) ABSTRACT

A unitary intravascular microcatheter with a continuous embedded helical coil reinforcement member and a method for making same are provided. Multiple catheters are manufactured from a continuous feedstock to reduce manufacturing time and labor cost. A selected length of a cylindrical tube is held stationary between a pair of spaced apart chuck members while a reinforcement wire is wrapped onto the stationary portion. The wire wrap portion of the cylindrical tube is advanced relative to the chuck members to hold a second selected length of no-wrap cylindrical tube stationary for wire wrapping of the second portion. The steps of advancing the cylindrical tube through the chuck members and then wrapping the reinforcement wire onto the tube is repeated for substantially the entire length of the elongate cylindrical tube to form a wire wrapped cylindrical tube with multiple wire wrapped sections spaced from one another by unwrapped sections. A coating of a continuous finish coating is then applied to the entire length of the wire wrapped cylindrical tube. The finish coated cylindrical tube is then cut to catheter lengths at selected locations and thereafter ground to a desired diameter and finish.

10 Claims, 6 Drawing Sheets

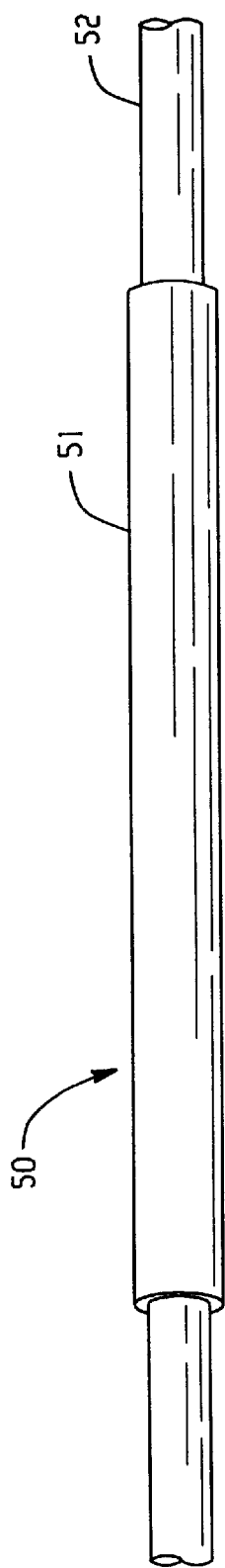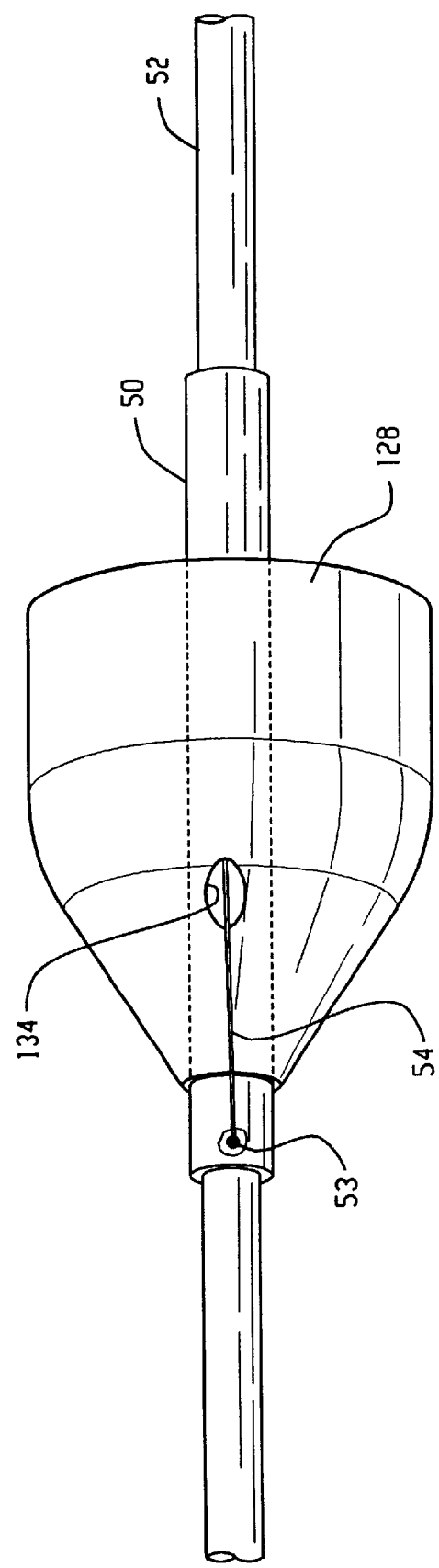

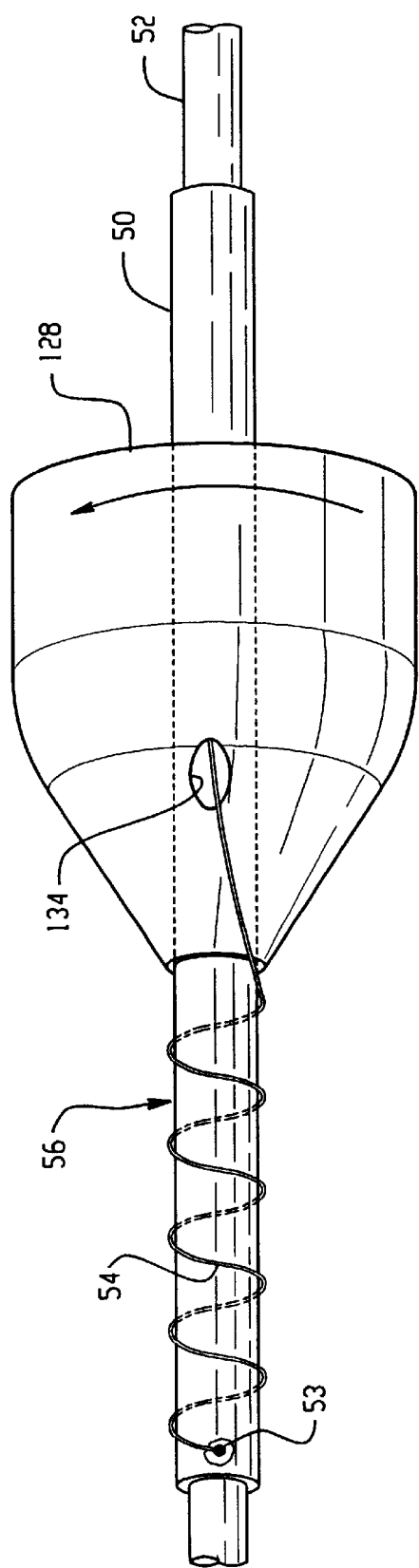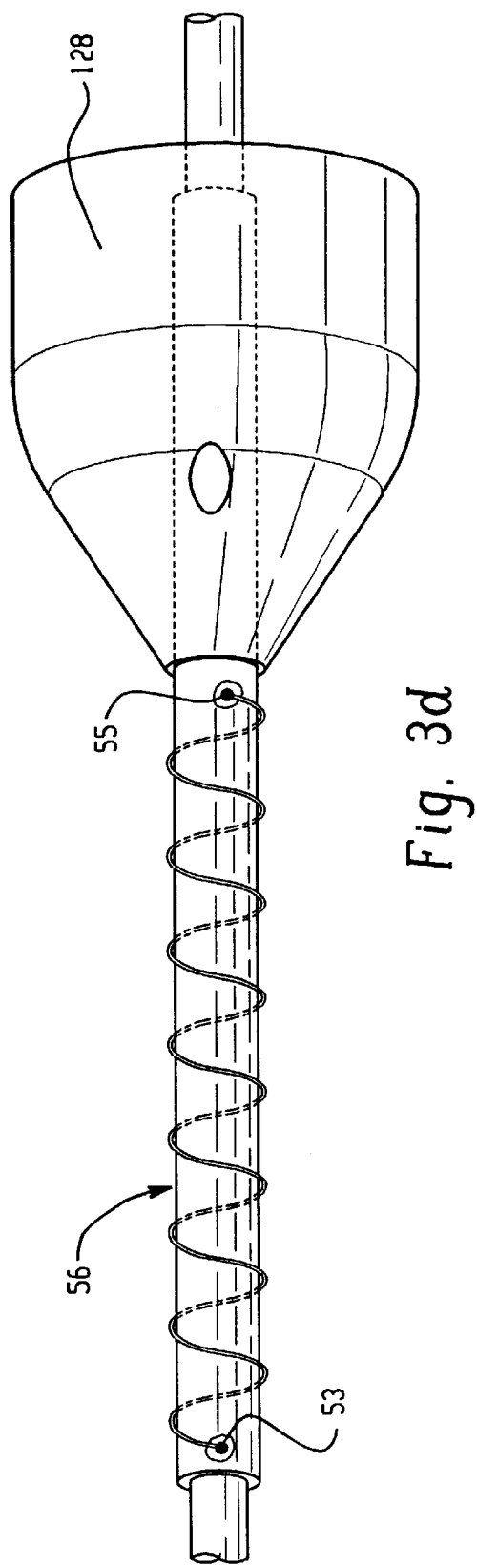
Fig. 3c
Fig. 3d

INTRAVASCULAR MICROCATHETER WITH EMBEDDED HELICAL COIL REINFORCEMENT MEMBER AND METHODS AND APPARATUS FOR MAKING SAME

BACKGROUND OF THE INVENTION

The subject invention is directed toward the art of vascular catheters and to catheter manufacturing methods and, more particularly, to intravascular microcatheters of unitary construction provided with an integral continuous coiled wire reinforcement member, and to improved methods and apparatus for manufacturing multiples of such catheters from a continuous feedstock.

Angiographic catheters have been widely used for diagnostic purposes such as in conjunction with the injection of dyes or the like into arteries for the visualization of obstructions, ruptures, or other malformations. Diagnostic catheters are typically constructed with an embedded layered wire braid reinforcement system surrounding the lumen to provide torsional control and to strengthen the catheter body to better withstand high pressure injections.

Catheters of the type described above are shown in my prior U.S. Pat. No. 3,485,234, which issued Dec. 23, 1969. My prior U.S. Pat. No. 3,585,707, which issued Jun. 22, 1971 sets forth generally a method of manufacturing wire braid type angiographic catheters. In addition, my prior U.S. Pat. Nos. 5,738,742 and 5,972,143 describe how to manufacture a plurality of diagnostic catheters having unitary body and tip sections from a continuous feedstock. The teachings of the above prior patents are incorporated herein by reference.

It is likely that wire braid construction will continue to be useful in larger diameter catheters such as in the size range French 8 through French 4. However, in modern medical practice, the use of catheter device has been broadened to embrace many forms of interventional therapy. As examples, catheters are presently used in connection with placement of dilation balloons for opening obstructed coronaries and other vessels, for the placement of stints to "prop" open vessels, for introduction of anticoagulants to dissolve clots, and for introduction of coagulants to form clots to "plug" aneurysms or to seal off vessels feeding malignant tumors. The target vessels in the above procedures are typically located in the smaller vessels of the brain, kidney, liver, heart, and other organs. Braided wire catheters, however, are not well suited for applications that require a catheter size of French 3 or smaller. There is a need, therefore, for much smaller catheters that can be extended into the smaller target vessels.

One solution is to construct a catheter that uses a coiled wire reinforcement member within the catheter body as an alternative to the braided wire reinforcement construction scheme. Although the coiled wire construction results in some loss of torsion control, a significantly thinner overall catheter body is enabled. Catheters that include integral coiled wire members have an overall good pushability characteristic and typically do not kink as readily as braided wire construction catheters of the same diameter using the same wire diameter.

Another advantage is that coiled reinforcement wire catheters can provide a larger lumen size than braided wire type catheters relative to overall catheter body size. Since the reinforcement wire is overlapped in the braided construction as it is braided onto the inner catheter wall construction, the overall reinforcement layer thickness is at least twice as large as in the non-overlapping coiled wire type catheter using the same wire diameter.

U.S. Pat. Nos. 5,733,400 and 5,662,622 teach an intravascular catheter carrying a helical reinforcement member embedded within at least a portion of a tubular wall of the catheter. The catheter body is formed from separate sections which are connected end to end to provide successively increasing flexibility zones from the proximal end toward the distal catheter end. The catheter body is thin and therefore particularly capable of being advanced into small areas such as brain arteries for example, so that therapeutic agents may be delivered to locations deep inside the brain, which locations would be inaccessible to many other catheters.

However, the catheter taught in the above patents is expensive because the manufacturing method is very labor intensive. More particularly, turning to the flowchart illustrated in FIG. 1, the prior art manufacturing process 10 includes the steps of joining together a pair of tubular catheter reinforcement members in end-to-end, abutting relation 12. Next, in step 14, a UV curable adhesive is placed on the joined ends. In step 16, the joined ends are covered with a snug, non-adherent transparent sleeve. The adhesive is cured in step 18 and, thereafter, in step 20, the cover sleeve is removed. Additionally, preferably, the adhesive is cured using ultraviolet light and, accordingly, the sleeve is formed of a substantially ultraviolet radiation transparent material. In step 22, the joined reinforcement members are embedded into a tubular plastic catheter wall.

One major disadvantage of the catheter construction and method taught in the above patents is that the manufacturing method is highly time consuming and labor intensive. Further, the overall catheter assembly could be prone to failure because it is formed of a plurality of joined individual parts.

Accordingly, it would therefore be desirable to provide an interventional therapy type catheter having a continuous coil reinforcement member and that is of a substantially unitary construction. Further, it would be desirable to provide methods and apparatus for manufacturing multiples of such catheters from a single feedstock using a continuous process. In order to reduce manufacturing cycle time, it is desirable to wind the reinforcement wire directly onto the inner substrate layer of the catheter body in a continuous manner and, thereafter, apply one or more subsequent catheter body layers to produce a large number of catheters from a single feedstock in an efficient manner with minimal labor demands.

SUMMARY OF THE INVENTION

The subject invention provides a unitary intravascular microcatheter with a continuous embedded helical coil reinforcement member and methods and apparatus for manufacturing same at a reduced manufacturing cost by enabling multiple catheters to be manufactured from a continuous feedstock. The overall construction of the subject microcatheter device is unitary, making the subject device less prone to failure and easy to manufacture in multiples. The embedded reinforcement member forms a continuous helical path along the length of the microcatheter with a selected variable pitch angle to control the stiffness of the microcatheter at various portions. The pitch of the reinforcement member winding is selectively varied along the length of the catheter to provide a smooth transition between different catheter stiffness regions.

In accordance with a preferred aspect of the invention, there is provided methods and apparatus for manufacturing multiple catheters from a continuous feedstock. A selected length of an elongate cylindrical tube is provided, preferably, carried on an inner wire mandrel to prevent the tube from collapsing during the various manufacturing operations. A first selected length of the cylindrical tube is held stationary between a pair of spaced apart chuck members. A lead end of a reinforcement wire is spot-bonded to the tube and then wrapped onto the stationary portion of the first selected length of the cylindrical tube. The trailing end of the reinforcement wire is thereafter spot-bonded to the tube. The wire wrapped portion of the cylindrical tube is then advanced relative to the pair of spaced apart chuck members to hold a second selected length of non-wire wrapped cylindrical tube stationary between the pair of chuck members. The reinforcement wire is then spot-bonded and wrapped onto a portion of the second selected length of the cylindrical tube held between the spaced apart chuck members using the procedure described above. The steps of advancing the cylindrical tube through the chuck members and then wrapping the reinforcement wire onto the tube is repeated for substantially the entire length of the elongate cylindrical tube to form a wire wrapped cylindrical tube with multiple wire wrapped sections spaced from one another by unwrapped sections. A continuous finish coating is then applied to the wire wrapped cylindrical tube. Lastly, the coated wire wrapped cylindrical tube is divided into multiple catheters by cutting the coated wire wrapped cylindrical tube at locations corresponding to unwrapped sections (i.e. sections without reinforcement wire wrapping) of the elongate cylindrical tube.

In its preferred form, the reinforcement wire is wrapped onto the cylindrical tube in a helical form along a path at selected angles relative to a plane perpendicular to a longitudinal axis defined by the cylindrical tube to provide regions of selected stiffness along the length of the catheter.

In accordance with a further aspect of the invention, the reinforcement wire is wrapped onto the cylindrical tube to form helical patterns in each of the catheters having a plurality of helical portions including at least helical first and second portions, the helical first portion having coils of a first pitch and the helical second portion having coils of a second pitch different than the first pitch. In that way, intravascular catheters are formed having portions of selected different flexibility characteristics.

In accordance with still a further aspect of the invention, there is provided a method and apparatus for manufacturing multiple catheters from a continuous feedstock. A selected length of an elongate cylindrical tube is provided, preferably, carried on an inner wire mandrel to prevent the tube from collapsing during the various manufacturing operations. A first selected length of the cylindrical tube is held taut between a pair of spaced apart reels including a tube pay-out reel and a tube take-up reel. A reinforcement wire is wrapped onto the cylindrical tube as the tube is advanced between the pair of spaced apart reels. The steps of advancing the cylindrical tube relative to the spaced apart reels and wrapping the reinforcement wire onto the tube are executed substantially simultaneously. The wrapping and advancing steps continue simultaneously, preferably for the entire length of the elongate cylindrical tube to form a wire wrapped cylindrical tube having a reinforcement wire wrapped in a helical form along a path at selected angles relative to a plane perpendicular to a longitudinal axis defined by the cylindrical tube to provide regions of selected stiffness along the length of the catheter. A continuous finish coating is applied to the wire wrapped cylindrical tube to hold the reinforcement wire on the tube and to form a coated wire wrapped cylindrical tube. Lastly, the coated wire wrapped cylindrical tube is divided into multiple catheters by cutting the coated wire wrapped cylindrical tube at selected locations.

In accordance with yet a further aspect of the invention, an intravascular catheter device is provided including an elongate flexible tubular inner wall defining a lumen of the catheter. The inner wall includes a first end defining a proximal end of the intravascular catheter and a second end defining a distal end of the intravascular catheter. A continuous coil reinforcement member is carried on the elongate flexible tubular inner wall and extends between the proximal end of the catheter and the distal end of the catheter. An elongate flexible tubular outer wall is provided covering the coil reinforcement member and carried on the inner wall substantially entirely between the proximal end of the catheter and the distal end of the catheter. In order to provide an intravascular catheter having portions with selected flexibility, the continuous coil reinforcement member is carried on the elongate flexible tubular inner wall along a helical path at selected varied angles relative to a plane perpendicular to the longitudinal axis defined by the catheter. Open helical winding pattern portions of the coil reinforcement member define flexible catheter portions. Conversely, closed helical pattern portions of the coil reinforcement member define relative stiff portions of the intravascular catheter. The pitch of the helical winding pattern is continuously selectively varied to provide a smooth transition between stiff and flexible regions along the length of the catheter.

The primary object of the invention is a reduction in the cost and time associated with manufacturing intravascular catheters with embedded helical coil reinforcement members.

Yet another object of the invention is the provision of an inexpensive intravascular microcatheter having a unitary construction that is less prone to failure during use. The microcatheter of the subject invention includes a continuous embedded helical coil reinforcement member that extends substantially between the proximal and distal ends of the catheter body.

A still further object of the invention is the provision of an apparatus for manufacturing intravascular microcatheters with embedded helical coil reinforcement members from a continuous feedstock.

Still other objects, advantages, and benefits of the invention will become apparent to those skilled in the art upon a reading and understanding of the following detailed description.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein:

FIGS. 3a–3f are views in side elevation of multiple catheters formed in accordance with the present invention from a continuous feedstock shown in various stages of sequential construction;

DETAILED DESCRIPTION OF THE PREFERRED EMBODIMENTS

Figure 1:
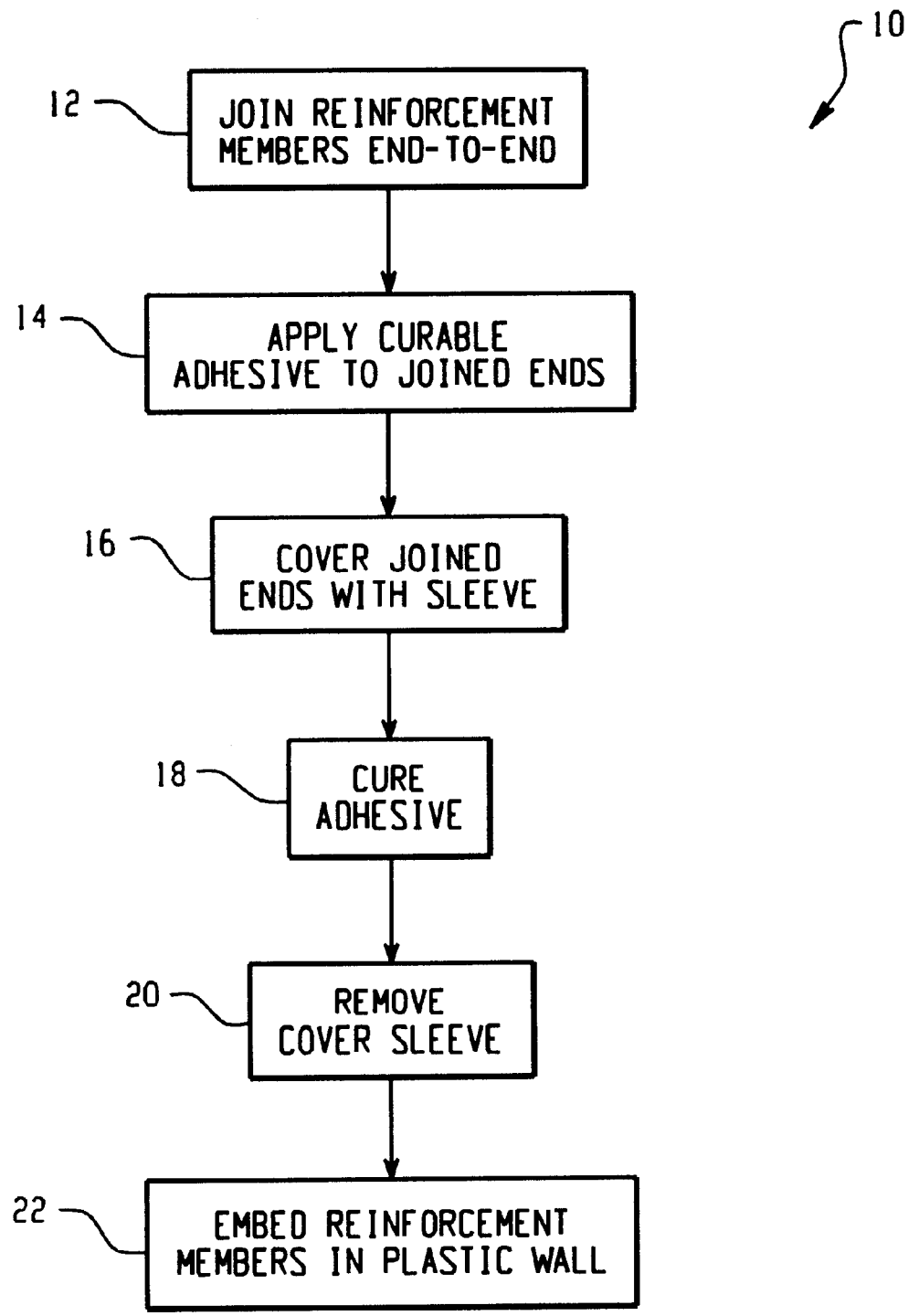
FIG. 1 is a flow chart showing a typical prior art processing method used for manufacturing catheters with coiled reinforcement members.
Figure 2:
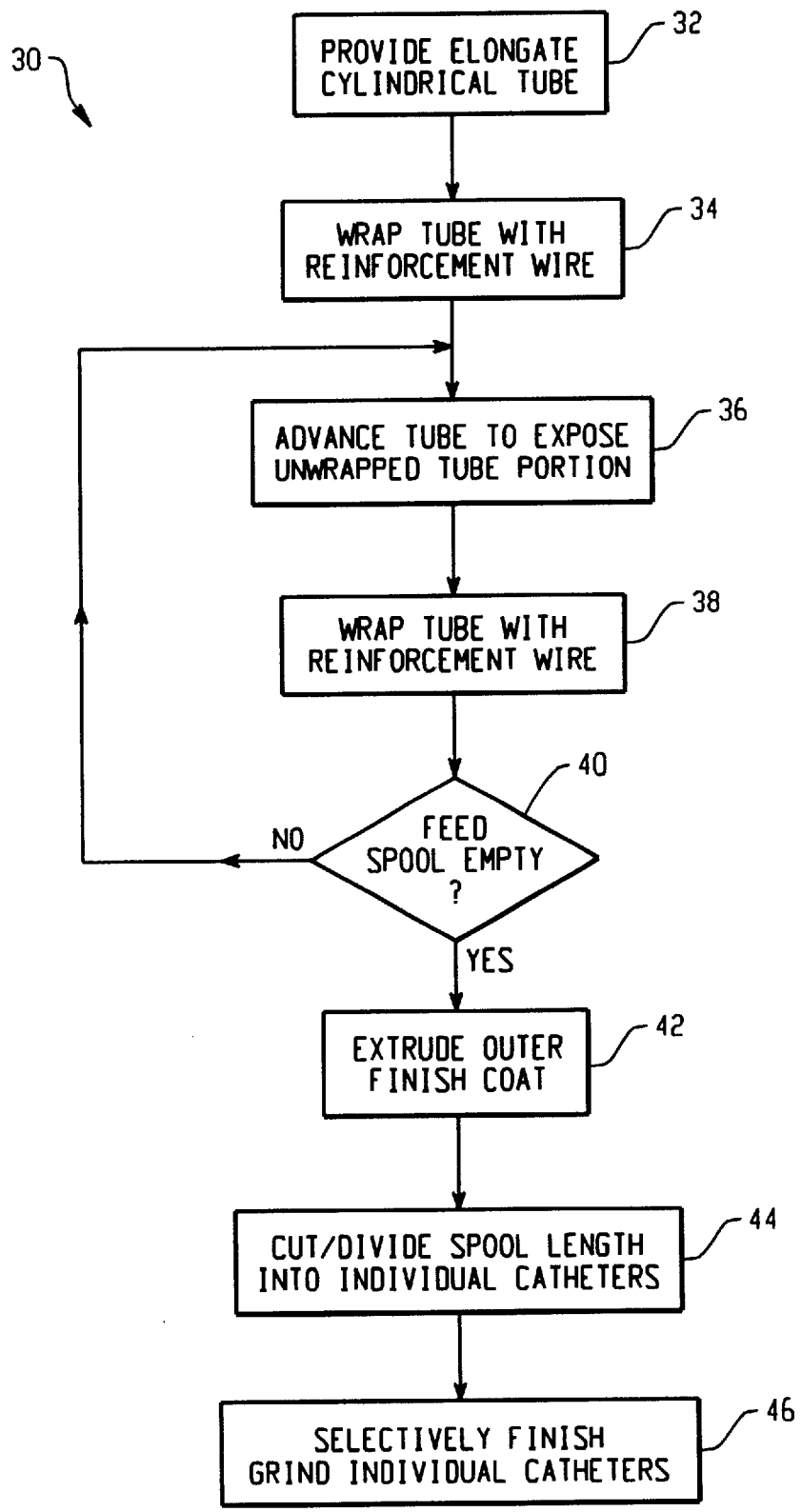
FIG. 2 is a flow chart showing a method for manufacturing multiple catheters with a coiled reinforcement member from a continuous feedstock in accordance with the present invention.

Referring now to the drawings wherein the showings are for the purposes of illustrating the preferred embodiments of the invention only and not for purposes of limiting same, FIG. 2 shows a flow chart illustrating the preferred method 30 of manufacturing an intravascular catheter with a helical coil reinforcement member. The full sequence of steps for the preferred embodiment of the inventive process are set forth in relative diagrammatic form in FIGS. 3a–3f. The side elevational views of the catheter shown in FIGS. 3a–3f in various stages of construction correspond to a greater or lesser degree with the manufacturing method steps illustrated in FIG. 2. It will be noted in comparing FIG. 2 to the prior art manufacturing process shown in FIG. 1 and previously described above that the present invention does not require manual attachment of portions of the catheter in an end-to-end abutment relationship. Rather, the entire sequence of steps involves a progressive processing of what is essentially a single element.

As shown in FIG. 2, the preferred manufacturing method 30 includes the initial step 32 of providing a selected length of an elongate cylindrical tube. Preferably, an elastomeric tube 50 (FIG. 3a) is provided carried on a wire mandrel having an outer diameter that corresponds to the desired lumen diameter of the catheter to be made. As an example, for a French 3 size, the nominal lumen diameter is 0.022 inches. The elastomeric body tube 50 could be formed in many ways, but, in the preferred form of the invention, it is formed by extruding a desired elastomeric material 51 such as a relatively soft plastic or polyurethane onto a wire mandrel 52 or onto a monofilament mandrel made of a suitable plastic having the desired lumen diameter. In the preferred embodiment illustrated, the mandrel 52 is formed of silver plated copper.

One material that has been found to be particularly well suited for use as a catheter tube body is Pellethane, a urethane produced by Dow Chemical. In addition, other materials have been found to be adequately well suited such as nylon materials including PEBAX available from Dow Chemical. The wire mandrel used can have substantially any desired length, but is preferably a substantial number of multiples of the desired final length of the catheter bodies being formed. As an example, it is advantageous to construct multiple catheter tube bodies onto a continuous reel of one thousand feet (1,000 ft.) or more of mandrel feedstock. For catheters having a nominal length of sixty inches (60 in.), the present invention yields as many as one hundred sixty-six (166) catheters from a single roll of feedstock.

According to the preferred manufacturing method, the entire length, preferably one thousand feet (1,000 ft.) of wire or monofilament which is to function as the mandrel in the formation of the basic elastomeric body tube is passed through a conventional extruder to coat the mandrel with a selected thickness, preferably a layer of between 0.002–0.003 inches of elastomer 51 which may vary slightly depending upon the size of the catheter being made. Thereafter, in a wire wrapping step 34, the elastomeric tube 50 (FIG. 3a), preferably the entire one thousand foot (1,000 ft.) length, with the mandrel in place, is passed through a winding apparatus 100 to be described in detail below for overlaying the elastomeric body tube 50 with a single strand of a small diameter reinforcement wire 54 to form a composite coiled structure 56 (FIG. 3c). Preferably, the reinforcement member is a thin stainless steel wire with a preferred diameter of 0.002 inches.

In accordance with the preferred method of the invention, the elastomeric tube 50 is held stationary while the wire reinforcement member 54 is wound thereon in a substantially helical form as shown in FIG. 3c. This enables unwrapped portions of the elastomeric tube 50 to be held on large spools on a pay-out end 106 of the winding apparatus shown in FIG. 5 and further, enables wire wrapped portions of the elastomeric tube to be collected in a take-up end 108 of the winding apparatus. Generally, the winding apparatus 100 includes a pay-out spool 102 and a take-up spool 104 on opposite pay-out and take-up ends 106, 108 of a frame member 110, respectively. A pair of clamping chucks 112, 114 are supported on the frame member 110 by respective first and second support members 116, 118, respectively. Preferably, in accordance with the invention, each of the clamping chucks 112, 114 are adapted to selectively clamp selected portions of the elastomeric tube 50 therebetween, preferably, a length of about six (6) feet. In that way, the elastomeric tube is held stationary between the clamping chucks 112, 114 while the wire reinforcement member 54 is wrapped thereon at step 34 (FIG. 2).

Figure 4:
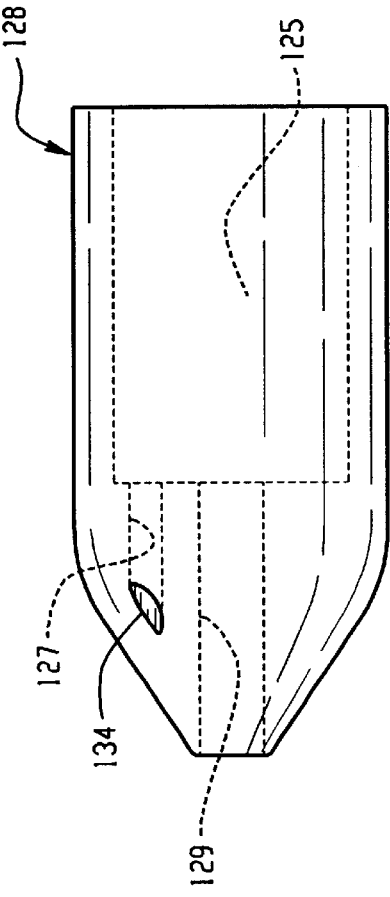
FIG. 4 is a side elevational view of the coiler tip device for winding the reinforcement wire onto the cylindrical tube as shown in FIGS. 3a–3f; and, FIG. 5 is a diagrammatic view of a winder device for manufacturing a plurality of catheters with coiled reinforcement members from a continuous feedstock in accordance with the present invention.
Figure 5:
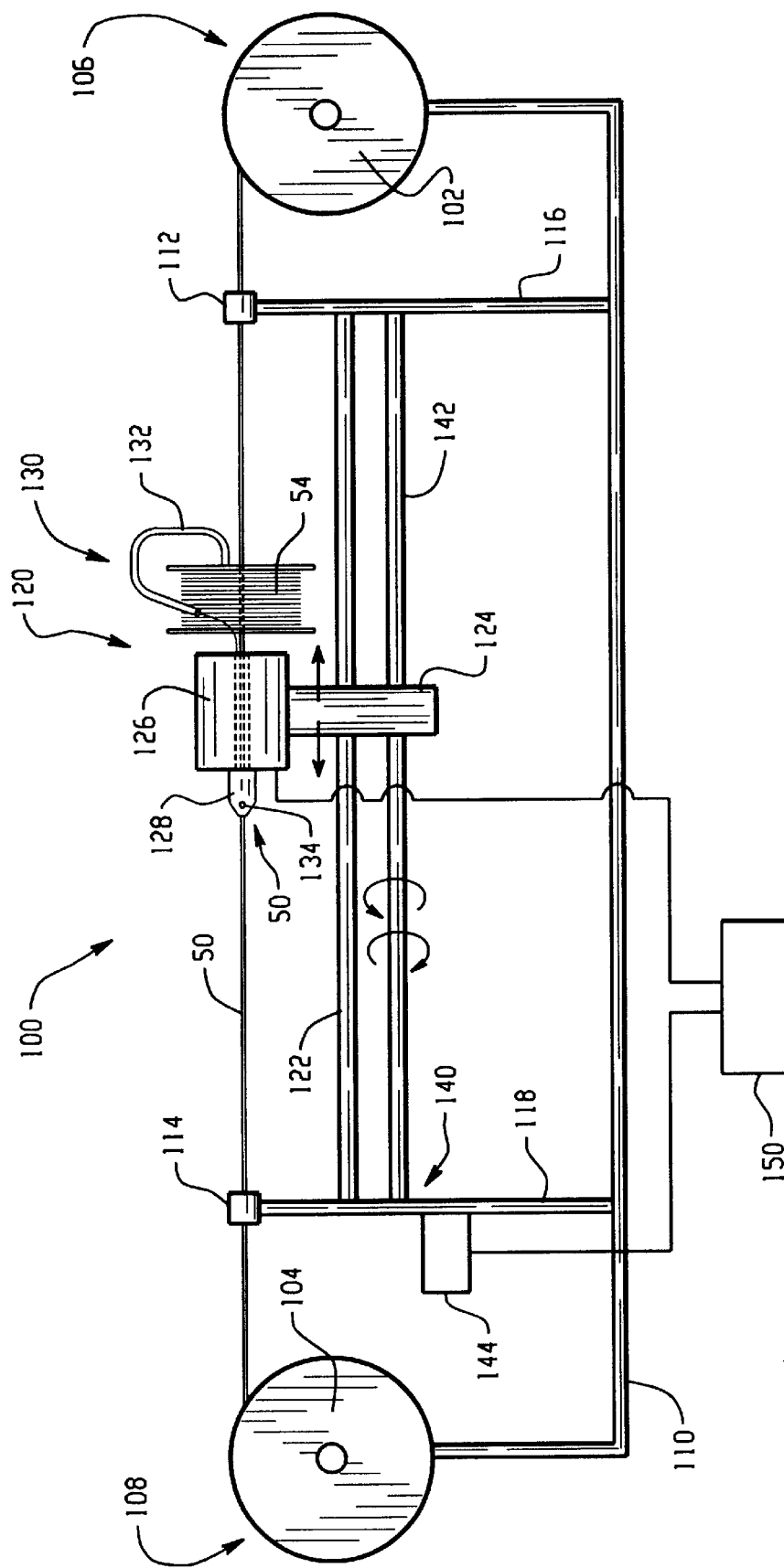

With continued reference to FIG. 5, a winder shuttle 120 is slidably attached to a guide beam member 122 of the frame 110. Preferably, the winder shuttle 120 includes a relatively rigid lower attachment member 124, an electric winding motor 126 with a rotatable coiler tip member 128 and wire spool 130 on opposite sides of the winder motor 126. A hollow J-tube member 132 is preferably attached to the coiler tip 128 and supported for rotational movement relative to the wire spool 130 and the winding motor 126. Preferably, the winding motor 126 includes a hollow output drive shaft connected to the coiler tip 128 and J-tube member 132 so that the portion of elastomeric tube 50 supported between the clamping chuck members 112, 114 can be threaded through the winder shuttle 120. As best shown in FIGS. 3c and 4, a lead end 53 of the wire reinforcement member 54 extends through a hollow body portion 127 of the coiler tip 128, through an offset bore 127 and out from the coiler tip through an offset opening 134. A substantially cylindrical bore 129 extends along the longtudinal axis of the winder tip is shown and is adapted to receive the cylindrical tube therein in a manner shown in FIGS. 3b–3d. The free end of the reinforcement member 54 is first attached to the elastomeric tube 50 near the clamping chuck 114 at the take-up end 108 by spot-bonding 53 preferably using a UV curable adhesive, or the like. A small opening 134 is provided in the coiler tip 128 as shown to enable the wire reinforcement member 54 to feed off from the wire spool 130 (FIG. 5) and then successively through the J-tube member 132, winding motor 126, and coiler tip 128 substantially as shown. As the winding motor 126 rotates, the wire reinforcement member 54 is payed out from the wire spool 130 and wrapped onto the elastomeric tube 50 held stationary between the clamping chucks 112, 114.

In order to provide a helical pattern to the wire reinforcement member 54 as it is wrapped onto the stationary elastomeric tube 50, a translation system 140 is provided.

Preferably, the translation system includes a threaded lead screw 142 rotatably carried on opposite ends on the first and second vertical support members 116, 118, respectively. The lead screw 142 is selectively rotatable using a translation motor 144 attached directly to the lead screw. Preferably, the lower attachment member 124 of the winder device 120 includes a transverse opening having internal threads that correspond with the size and pitch of the threads provided on the lead screw 142. In that way, rotation of the lead screw 142 causes the winder device 120 to slide along the guide beam member 122 to the left and right as illustrated in FIG. 5.

Preferably, a control mechanism 150 is provided in the subject winding apparatus 100 to enable coordinated motion between the winding motor 126 and the translation motor 144. In that way, the pitch of the wire reinforcement member 54 wrapped onto the stationary elastomeric tube 50 is selectively controlled to produce the desired stiffness/flexibility characteristics along the length of the finished catheter device. As an example, in order to produce a flexible region in the catheter, the pitch of the wire reinforcement member winding pattern is increased by either reducing the speed of the winding motor 126, or increasing the speed of the translating motor 144, or both. Conversely, in order to increase the stiffness or decrease the flexibility in the catheter, the pitch of the wire reinforcement member is decreased by increasing the speed of the winding motor 126 or reducing the speed of the translating motor 144, or both.

With reference once again to FIG. 2, the preferred method of manufacturing multiple catheters from a continuous feedstock includes the step of advancing the elastomeric tube 50 from the pay-out end 106 of the winding apparatus 100 toward the take-up end 108. At step 36, the wire wrapped elastomeric tube portion is advanced from between the clamping chucks 112, 114 and wound onto the take-up spool 104. This presents fresh unwrapped elastomeric tube 50 between the spools 102, 104 taken from the pay-out spool 102. Thereafter, the clamping chucks 112, 114 are tightened onto the elastomeric tube 50 to hold it stationary in place relative to the winder device 120. Thereafter, the winder device 120 is positioned to the left as viewed in FIG. 5 for attachment of the lead end 53 of the wire reinforcement member 54 onto the elastomeric tube 50 such as shown in FIG. 3c. In wrapping step 38, the wire reinforcement member 54 is wound onto the stationary portion of the elastomeric tube 50 held between the clamping chucks 112, 114 by simultaneously activating the translation motor 144 and the winding motor 126 using the control device 150. The trailing end 55 of the wire reinforcement member 54 is similarly attached to the elastomeric tube 50 by spot-bonding preferably using UV curable adhesive, or the like as shown in FIG. 3d. The portion of the wire reinforcement member between the trailing end 54 and the coiler tip 128 is cut so that the wound portion of the elastomer tube can be released from the clamping chucks 112, 114 for winding onto the take-up spool 104. The sequence of advancing the elastomeric tube 36 and wrapping the wire reinforcement member 38 onto the tube is repeated until, at step 40 the entire wire mandrel and elastomeric tube carried thereon is depleted from the pay-out spool 102. At this point in the preferred method, a wire wrapped cylindrical tube with multiple wire wrapped sections spaced from one another by unwrapped sections is formed and collected on the take-up spool 104. Preferably, a wire mandrel supporting the cylindrical tube having a nominal length of approximately one thousand feet (1,000 ft.), approximately one hundred sixty-six (166) wire wrapped sections are formed spaced from one another by unwrapped sections.

In the preferred method 30, a bonding coating is not used. However, a small amount of a bonding coating can be applied. Alternatively, a bonding coating can be applied continuously to the entire length of the cylindrical tube to provide a continuous means for attaching the wire reinforcement member 54 to the elastomeric tube 50. Alternatively again, the tension applied to the wire reinforcement member by the winder device 120 can be controlled using the winding motor 126 to embed the reinforcement member slightly into the elastomeric tube. As yet still another alternative, a bonding coating can be used together with tension control to ensure that the wire reinforcement member is tightly mechanically coupled to the elastomeric tube 50.

Figure 3E:
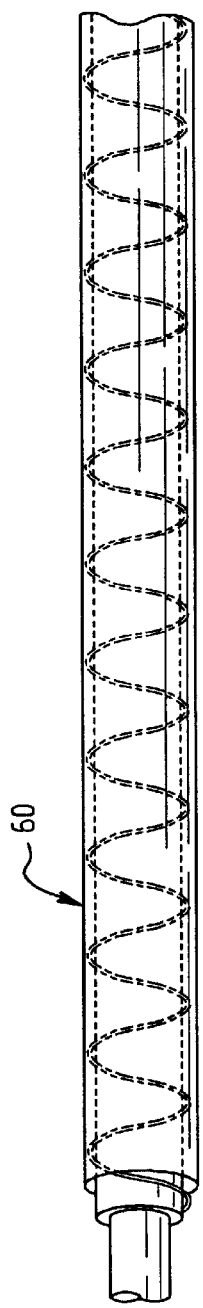
Figure 3F:
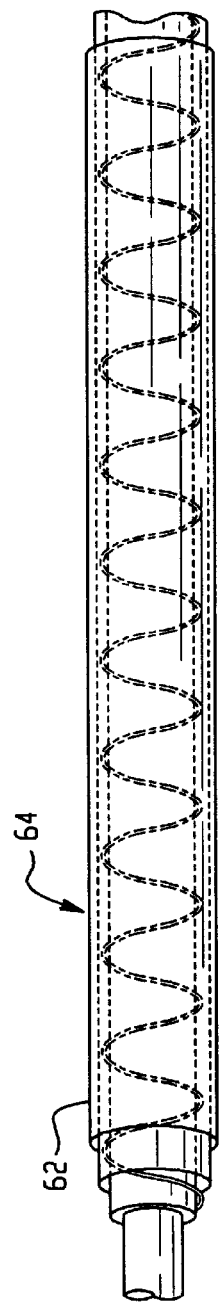

In step 42, the entire length of the wire wrapped cylindrical tube 60 (FIG. 3e) is coated with a predetermined thickness of a continuous finish coating 62 to form a finish coated wire wrapped cylindrical tube 64 (FIG. 3f).

Lastly, after the finish coated wire wrapped cylindrical tube 64 is formed in step 42, the tube is cut or divided in step 44 at appropriate locations to produce individual catheters having the length and other properties desired. In order to provide a suitable exterior finish surface to the catheters they may be ground individually in catheter lengths at step 46.

In accordance with an alternative method of the invention, the elastomeric tube 50 is held taut between the pay-out spool 102 and the take-up spool 104 without the use of the above-described clamping chucks 112, 114. In this embodiment, the elastomeric tube 50 is passed from the pay-out spool 102 and onto the take-up spool 104 while the wire reinforcement member 54 is wrapped thereon. In that way, a continuous wrapping of the reinforcement wire 54 onto the elastomeric tube 50 is provided.

In the above alternative embodiment, in order to produce a flexible region in the catheter, the pitch of the wire reinforcement member winding pattern is increased by either reducing the speed of the winding motor 126 or increasing the speed of travel of the elastomeric tube 50 from the pay-out spool 102 to the take-up spool 104. Essentially, in this embodiment, the translation of the winding motor 126 and the spot-bonding steps are unnecessary. In the continuous coiling embodiment, there is no need to repeatedly stop and then continue the winding process between steps of applying the locking resin. Rather, there is no need to stop the winding operation until the entire length of the elastomeric tube 50 is fed from the pay-out spool 102 to the take-up spool 104 and wrapped with the wire reinforcement member therebetween.

As with the above preferred embodiment, the alternative method includes a control mechanism 150 provided to enable coordinated motion between the winding motor 126 and the translation of the elastomeric tube from the pay-out spool 102 onto the take-up spool 104. In that way, the pitch of the wire reinforcement member 54 wrapped onto the moving or translating elastomeric tube 50 is selectively controlled to produce the desired stiffness/flexibility characteristics along the entire length of the finished catheter device. As an example, in order to produce a flexible region in the catheter, the pitch of the wire reinforcement member winding pattern is increased by either reducing the speed of the winding motor 126, or increasing the speed of the moving elastomeric tube 50, or both. Conversely, in order to increase the stiffness or decrease the flexibility in the catheter, the pitch of the wire reinforcement member is decreased by increasing the speed of the winding motor 126 or reducing the speed of the moving elastomeric tube from the pay-out spool 102 onto the take-up spool 104.

Further in addition to the above, in the alternative preferred method, after the above-described continuous coiling operation for winding the wire reinforcement member onto the cylindrical-tube without interruption to form a wire wrapped cylindrical tube 60 (FIG. 3e), the entire length of the wire wrapped cylindrical tube is coated with a predetermined thickness of a continuous finish coating 62 to form a coated wire wrapped cylindrical tube 64 (FIG. 3f).

Thereafter, the coated wire wrapped cylindrical tube 64 is cut to catheter lengths at predetermined locations along the length of the coated composite cylindrical tube. The cut catheter lengths are thereafter selectively ground to size and finish. A portion of the distal section of each catheter is selectively ground to a reduced diameter relative to the main body portion to further enhance the flexibility of the catheter. The grinding operation is selectively a step grinding operation or a smooth long taper grinding operation. In addition, if additional flexibility is required, a tubular section of a very soft plastic material such as, for example, Pellethane 80A, a urethane product available from Dow Chemical, can be fused or molded onto the distal portion of the catheter. The fusing or molding process is preferably accomplished in a manner as described in my earlier U.S. Pat. No. 3,485,234.

The invention has been described with reference to the preferred embodiments. Obviously, modifications and alterations will occur to others.upon a reading and understanding of this specification. It is intended to include all such modifications and alterations insofar as they come within the scope of the appended claims or the equivalents thereof.

Having thus described the invention, it is claimed:

1. An intravascular catheter comprising:
   an elongate flexible tubular inner wall defining a lumen of the catheter, the inner wall having a first end defining a proximal end of the catheter and a second end defining a distal end of the catheter;
   a continuous metallic coil reinforcement member carried on the elongate flexible tubular inner wall and extending between the proximal end of the catheter and the distal end of the catheter; and,
   an elongate flexible tubular outer wall covering the metallic coil reinforcement member and the inner wall substantially entirely between the proximal end of the catheter and the distal end of the catheter.

2. The intravascular catheter according to claim 1 wherein:
   the lumen defines a longitudinal axis of said intravascular catheter; and,
   the continuous coil reinforcement member is carried on the elongate flexible tubular inner wall along a path to select varied angles relative to a plane perpendicular to said longitudinal axis of the catheter.

3. The intravascular catheter according to claim 2 wherein the continuous coil reinforcement member defines a helical pattern including at least first and second portions, the helical first portion having a first pitch relative to the plane perpendicular to said longitudinal axis and the helical second portions having a second pitch relative to the plane perpendicular to the longitudinal axis different than said first pitch.

4. The intravascular catheter according to claim 3 wherein:
   said first pitch is greater than said second pitch;
   the helical first portion defines a flexible region of the intravascular catheter; and,
   the helical second portion defines a region of the intravascular catheter less flexible than said flexible region.

5. The catheter according to claim 1 wherein:
   the continuous coil reinforcement member extends substantially the entire length between said proximal end of the catheter and said distal end of the catheter.

6. The catheter according to claim 1 wherein:
   the continuous coil reinforcement member forms a continuous helical path along the length of the catheter with variable pitch angles to control the stiffness of the catheter at selected locations along the length of the catheter.

7. The catheter according to claim 1 wherein:
   the continuous coil reinforcement member is disposed on said inner wall forming a continuous helical path with a pitch relative to a longitudinal axis of the catheter selectively varied along a length of the catheter to form regions along the length of the catheter having respective different stiffnesses.

8. The catheter according to claim 1 wherein:
   the continuous coil reinforcement member is disposed in said continuous helical path to provide a smooth transition between different catheter stiffness regions.

9. An intravascular catheter comprising:
   an elongate flexible tubular inner wall defining a lumen of the catheter, the inner wall having a first end defining a proximal end of the catheter and a second end defining a distal end of the catheter;
   continuous metallic coil reinforcement member carried on the elongate flexible tubular inner wall and extending substantially the entire length between the proximal end of the catheter and the distal end of the catheter;
   an elongate flexible tubular outer wall covering the metallic coil reinforcement member and the inner wall substantially entirely between the proximal end of the catheter and the distal end of the catheter;
   said flexible tubular outer wall has a first outside diameter at said proximal end of the catheter and a second outside diameter at said distal end of the catheter; and, said second outside diameter is less than said first outside diameter.

10. The intravascular catheter according to claim 9, wherein: said outside diameter of said flexible tubular outer wall continuously tapers from said first outside diameter to said second outside diameter between the proximal end of the catheter and the distal end of the catheter.

* * * * *